United States Patent [19]

Cascales et al.

[11] Patent Number: 5,663,193
[45] Date of Patent: Sep. 2, 1997

[54] INHIBITORS OF FARNESYL-PROTEIN TRANSFERASE

[75] Inventors: Carmen Cascales, Madrid, Spain; Russell B. Lingham, Watchung, N.J.; Fernando Pelaez, Madrid, Spain; Jon D. Polishook, Cranford, N.J.; Keith C. Silverman, Somerset, N.J.; Sheo B. Singh, Edison, N.J.; Deborah L. Zink, Manalapan, N.J.

[73] Assignee: Merck & Co., Inc., Rahway, N.J.

[21] Appl. No.: 682,248

[22] Filed: Jul. 17, 1996

Related U.S. Application Data

[60] Provisional application No. 60/001,414 Jul. 25, 1995.
[51] Int. Cl.$^6$ ............... A61K 31/535; C07D 493/04
[52] U.S. Cl. ............... 514/450; 514/908; 549/349; 435/254.1
[58] Field of Search ............... 549/349; 514/450

[56] References Cited

U.S. PATENT DOCUMENTS

| | | |
|---|---|---|
| 5,082,489 | 1/1992 | Watson et al. . |
| 5,141,851 | 8/1992 | Brown et al. . |
| 5,151,529 | 9/1992 | Sato et al. . |
| 5,238,922 | 8/1993 | Graham et al. . |
| 5,245,061 | 9/1993 | Singh . |
| 5,254,727 | 10/1993 | Dufresne et al. . |
| 5,260,465 | 11/1993 | Singh et al. . |
| 5,260,479 | 11/1993 | Singh . |
| 5,310,949 | 5/1994 | Dufresne et al. . |
| 5,326,773 | 7/1994 | Desolms et al. . |
| 5,340,828 | 8/1994 | Graham et al. . |
| 5,352,705 | 10/1994 | Deana et al. . |
| 5,364,948 | 11/1994 | Harris et al. . |
| 5,420,157 | 5/1995 | Singh et al. . |
| 5,498,627 | 3/1996 | Ishii et al. . |
| 5,510,371 | 4/1996 | Singh et al. . |
| 5,534,537 | 7/1996 | Ciccarone et al. . |

FOREIGN PATENT DOCUMENTS 124777  9/1989  Japan .

OTHER PUBLICATIONS

Gibbs, J.B., et al., "Selective Inhibition of Farnesyl–Protein Transferase Blocks Ras Processing In Vivo," The Jour. of Biol. Chem., vol. 268, No. 11, pp. 7617–7620 (1993).
Goldstein, J.L., et al., "Nonfarnesylated Tetrapeptide Inhibitors of Protein Farnesyltransferase," The Jour. of Biol. Chem., No. 24, pp. 15575–15578 (1991).
James, G.L., et al., "Benzodiazepine Peptidomimetics:Potent Inhibitors of Ras Farnesylation in Animal Cells", Science, vol. 260, pp. 1937–1942 (1993).
Kohl, N.E., et al., "Protein Farnesyltransferase Inhibitors Block the Growth of Ras–dependent Tumors in Nude Mice", Proc. Natl. Acad. Sci., USA, vol. 91, pp. 9141–9145 (1994).
Kohl, N.E., et al., "Selective Inhibition of Ras–Dependent Transformation by a Farnesyltransferase Inhibitor", Science, vol. 260, pp. 1934–1937 (1993).
Pompliano, D.L., et al., "Steady–State Kinetic Mechanism of Ras Farnesyl:Protein Transferase", Biochemistry, vol. 31, pp. 3800–3807 (1992).
Qian, T., et al. "Design and Structural Requirements of Potent Peptidomimetic Inhibitors of p21 Ras Farnesyltransferase", The Jour. of Biol. Chem., vol. 269, No. 17, Issue of Apr. 29, pp. 12410–12413 (1994).
Reiss, Y., "Inhibition of Purified p21ras Farnesyl: Protein Transferase by Cys–AAX Tetrapeptides", Cell, vol. 62, pp. 81–88 (1990).
Reiss, Y., et al., "Sequences Requirement for Peptide Recognition by Rat Brain p21 Ras Protein Farnesyltransferase," Proc. Natl. Acad. Sci., USA, 88 pp. 732–736 (1991).
Schaber, M.D., et al., "Polyisoprenylation of Ras in Vitro by a Farnesyl–Protein Transferase", The Jour. of Biol. Chem., vol. 365, No. 25, pp. 14701–14704 (1990).
Schulz, S. and Nyce, J.W., "Inhibition of Protein Farnesyltransferase: A Possible Mechanism of Tumor Prevention by Dehydroepiandrosterone Sulfate," Carcinogenesis, vol. 15, No. 11, pp. 2649–2652 (1994).
Lorenzino, L.S., et al., "A Peptidomimetic Inhibitor of Farnesyl:Protein Transferase Blocks the Anchorage–dependent and independent Growth of Human Tumor Cell Lines," Cancer Research, vol. 55, pp. 5302–5309, Nov. 15, 1995.
Kohl, N.E., et al., "Inhibition of Farnesyltransferase Induces Regression of Mammary and Salivary Carcinomas in Ras Transgenic Mice," Nature Medicine, vol. 1, No. 8 (Aug. 1995).

*Primary Examiner*—Robert W. Ramsuer
*Attorney, Agent, or Firm*—Valerie J. Camara; Mark R. Daniel

[57]  ABSTRACT

The present invention is directed to non-peptide compounds which inhibit farnesyl-protein transferase (FPTase) and the farnesylation of the oncogene protein Ras. The invention also relates to the process for the preparation of a compound of this invention by cultivating a culture of Phoma sp. The invention is further directed to chemotherapeutic compositions containing the compounds of this invention and methods for inhibiting farnesyl-protein transferase and the farnesylation of the oncogene protein Ras.

11 Claims, No Drawings

INHIBITORS OF FARNESYL-PROTEIN TRANSFERASE

This application claims the benefit of U.S. Provisional application Ser. No. 60/001414 filed Jul. 25, 1995.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989)). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell,* 62:81–88 (1990); Schaber et al., *J. Biol. Chem.,* 265:14701–14704 (1990); Schafer et al., *Science,* 249:1133–1139 (1990); Manne et al., *Proc. Natl. Acad. Sci USA,* 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compounds dose. Reduction of farnesyl-protein transferase enzyme activity by adjusting the compounds dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., PNAS, 88:732–736 (1991)). Previously described CA$_1$A$_2$X-type FPTase inhibitors contain acyclic amino acids in the second position. Incorporation of proline in the A1 position in such inhibitors has been shown to be the least well tolerated amino acid substitution in that position (Reiss et al., PNAS (1991)). Such inhibitors may inhibit while serving as alternate substrates for the Ras farnesyl-transferase enzyme, or may be purely competitive inhibitors (U.S. Pat. No. 5,141,851, University of Texas).

Certain inhibitors of farnesyl-protein transferase selectively block the processing of Ras oncoprotein intracellularly (N. E. Kohl et al., *Science,* 260:1934–1937 (1993) and G. L. James et al., *Science,* 260:1937–1942 (1993)). Recently, it has also been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994)).

Inhibitors of farnesyl protein transferase which are citraconic acid derivatives have been isolated as fermentation products from a strain of Chaetomella acutiseta (U.S. Pat. No. 5,260,479 and EP-547671-A). Synthetic analogs of those compounds have also been described (U.S. Pat. Nos. 5,245,061 and 5,260,479).

Non-peptide compounds that are inhibitors of Ras farnesyl-protein transferase have been isolated from a strain of Cylindocarpon lucidum (U.S. Pat. No. 5,420,334).

Inhibitors of Ras farnesyl-protein transferase (FPTase) have been described in two general classes. The first are analogs of farnesyl diphosphate (FPP), while the second class of inhibitors is related to the protein substrate for the enzyme, Ras. Almost all of the peptide derived inhibitors that have been described are cysteine containing molecules that are related to the CAAX motif that is the signal for protein prenylation. An exception to this generalization is a class of natural products known as the pepticinnamins (Omura, et al., *J. Antibiotics* 46:222 (1993)).

It is, therefore, an object of this invention to develop a non-peptide compounds which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention relates to compounds which inhibit farnesyl-protein transferase and the farnesylation of the oncogene protein Ras, chemotherapeutic compositions containing the compounds of this invention, and methods for producing the compounds of this invention.

The compounds of this invention are illustrated by the following formula:

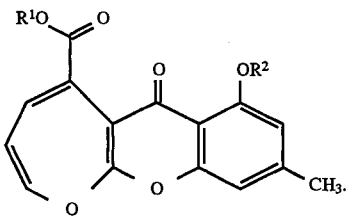

I

DETAILED DESCRIPTION OF THE INVENTION

The compounds of this invention are illustrated by formula I:

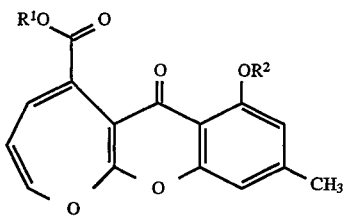

I wherein:

$R^1$ is H, or $C_1-C_4$ alkyl;

$R^2$ is H, $C_1-C_4$ alkyl, or —C(=O)$R^3$; and $R^3$ is $C_1-C_4$ alkyl;

or the pharmaceutically acceptable salt, hydrate or prodrug thereof.

In an embodiment of this invention, the compounds are illustrated by the formula:

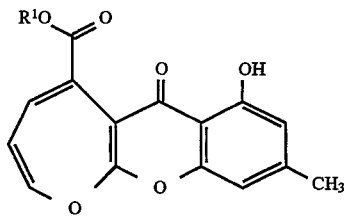

$R^1$ is H, or $C_1-C_4$ alkyl;

or the pharmaceutically acceptable salt, hydrate or prodrug.

In a second embodiment of this invention, the compounds are illustrated by the formula:

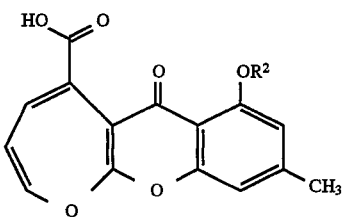

$R^2$ is H, $C_1-C_4$ alkyl, or —C(=O)$R^3$; and $R^3$ is $C_1-C_4$ alkyl;

or the pharmaceutically acceptable salt, hydrate or prodrug thereof.

The following are specific examples of the compounds of the instant invention, which include the pharmaceutically acceptable salt, hydrate or prodrug thereof. Compound A has the formula:

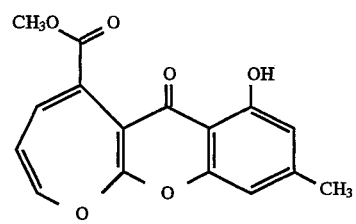

A

Compound B has the formula:

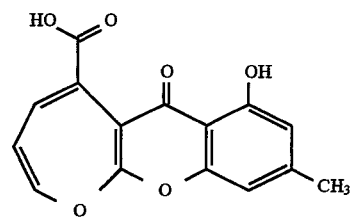

B

Compound H has the formula:

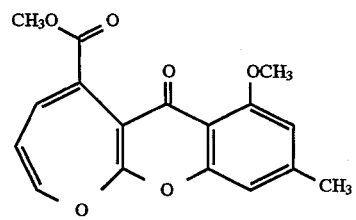

H

Compound I has the formula:

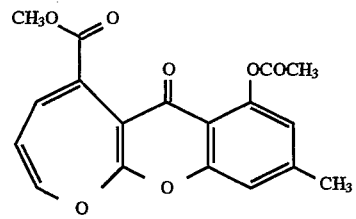

I

In the compounds of the present invention, combinations of substituents/or variables are permissible only as such combinations result in stable compounds.

As used herein, "alkyl" is intended to include both branched and straight-chain saturated aliphatic hydrocarbon groups having the specified number of carbon atoms. The term "alkyl" includes methyl, ethyl, propyl, iso-propyl, butyl, sec-butyl, tert-butyl and the like.

The compound A is prepared in an aerobic fermentation procedure employing a novel culture, MF 6118, identified as Phoma sp. Although the use of this organism is specifically described herein, mutants of the above described organism may also be capable of producing the compounds of this invention.

The culture MF 6118 is that of a fungus, Phoma sp., isolated from leaf litter of the desert shrub, Zygophyllum staffii, collected in Omdel, Namibia. This culture has been deposited with the American Type Culture Collection at 12301 Parklawn Drive, Rockville, Md. 20852 as ATCC 74347.

The culture MF 6118, identified as Phoma sp., exhibits the following morphological features:

On oatmeal agar (Difco Laboratories), colony attaining a diameter of 15 mm after about 7 days at about 25° C. and 67% relative humidity in 12 hr fluorescent photoperiod. Colony mat white, woolly, growing vertically 8 mm; margin white, entire; reverse a faint black; soluble pigment or exudate absent.

On potato-dextrose agar (Difco) colony attaining a diameter of 15 mm under the same environmental conditions. Colony mat white, cottony to woolly; margin hyaline, appressed, entire; reverse faint yellow, Pale Orange-Yellow (capitalized color names from Ridgway, R. 1912. Color Standards and Nomenclature, Washington, D.C.); soluble pigment or exudate absent.

On MYE (1% malt extract, 0.2 % yeast extract (both Difco)) colony attaining a diameter of 15 mm after 7 days under the same environmental conditions. Colony mat white, cottony; margin hyaline, entire; reverse faint yellow, Pale Yellow-Orange; soluble pigment or exudate absent; at 37° C. and in the dark, no growth.

On cornmeal agar (Difco) colony attaining a diameter of 16 mm under the same environmental conditions. Colony mat hyaline appressed with sparse cottony rafts near the margin; margin hyaline, entire; reverse, soluble pigment and exudate absent.

Conidiomata pycnidial, olivaceous to black, 100–300 µm, globose to subglobose, sometime irregular shaped with many ostioles, usually covered by a loose network of mycelium. Conidiogenous cells ampulliform, phialidic. Conidial exudate whitish cream. Conidia predominately elliptical, sometimes obovate, dumbbell shaped or cylindrical, hyaline, guttules at each end, 4–5×1–2 µm.

The key taxonomic characteristics of the fungal genus, Phoma (Coelomycetes, Deuteromycotina), include pycnidial conidiomata, enteroblastic, ampuliform conidiogenous cells, conidia that are hyaline, elliptical, guttulate and exuded in a mucoid mass. (B. Sutton. 1980. The Coelomycetes. Commonwealth Mycological Institute, Kew, Surrey, England. p 696.) MF 6118 exhibits all of the aforementioned generic characteristics but, in culture, does not exhibit any distinguishing characteristics to confidently place this fungus in a particular species. Therefore, it is designated as Phoma sp.

Compounds of this invention can be obtained by culturing the above noted fungus in aqueous nutrient media containing sources of assimilable carbon and nitrogen, preferably under aerobic conditions. Nutrient media may also contain mineral salts and defoaming agents.

The preferred sources of carbon in the nutrient medium are sucrose or fructose. The preferred sources of nitrogen are corn meal, and yeast extract.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organism which serves as seed in the production of the active compounds. After inoculation, the flasks are incubated with agitation at a temperature ranging from about 20°to 30° C., preferably about 22°to 25° C. Agitation rates may range up to 400 rpm, preferably about 200 to 220 rpm. Seed flasks are incubated over a period of about 2 to 10 days, preferably about 2 to 4 days. When growth is plentiful, usually about 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for about 3 to 30 days, preferably about 12 to 21 days. The fermentation is conducted aerobically at temperatures ranging from about 20°to 30° C. To obtain optimum results, the temperatures are in the range of about 22°to 28° C., most preferably about 22°to 25° C. After the appropriate period for production of the desired compound, fermentation flasks are harvested and the active compound isolated.

The farnesyl-protein transferase (FPTase) inhibition assay, presented below, measured the ability of the compound to inhibit Ras farnesylation in vitro. Recombinant human FPTase was used at 2 nM. In this assay, the ability to inhibit FPTase with a compound of this invention was demonstrated at a concentration of 10 µM or less.

In vitro inhibition of Ras farnesyl-protein transferase

Assays of farnesyl-protein transferase. Ras peptides (Ras-CVLS, Ras-CVIM and RAS-CAIL) were prepared as described by Schaber et al., *J. Biol. Chem.* 265:14701–14704 (1990) and Gibbs et al., *PNAS U.S.A.* 86:6630–6634 (1989), respectively. Recombinant human FPTase (rhFPTase) was prepared as described by Omer et al., (*Biochemistry* 32:5167–5176 (1993)) and was assayed in a volume of 100 µl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 0.1% (w/v) polyethylene glycol 20,000, 10 µM $ZnCl_2$, 50 nM [$^3$H]-farnesyl diphosphate ([$^3$H]-FPP; 740 CBq/mmol, New England Nuclear), 100 nM Ras-CVIM and 2 nM rhFPTase at 31° C. for 30 min. Reactions were initiated with FPTase and stopped with 100 µl of 30% (v/v) trichloroacetic acid (TCA) in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound.

Inhibitory activity of the compounds of the instant invention may also be measured with an assay employing the recombinant human FPTase obtained as described by C. A. Omer et al. (*Biochemistry*, 32:5167–5176 (1993)).

The pharmaceutical compositions containing the compounds of structural formula I inhibit farnesyl-protein transferase and the farnesylation of the oncogene protein Ras. The compounds is useful as a pharmaceutical agent for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of the chemotherapeutic compounds according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising the compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of the compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

The compounds of this invention may also be prepared according to the reactions as shown in the Reaction Schemes below, in addition to other standard manipulations such as ester hydrolysis, cleavage of protecting groups, etc., as may be known in the literature or exemplified in the experimental procedures.

REACTION SCHEME A

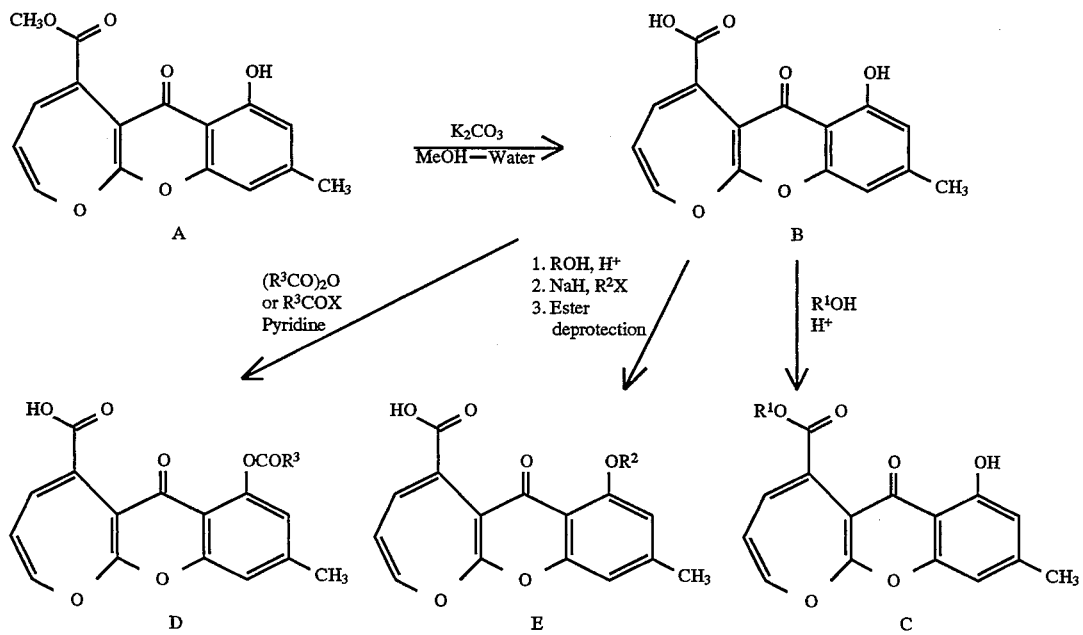

-continued
REACTION SCHEME A

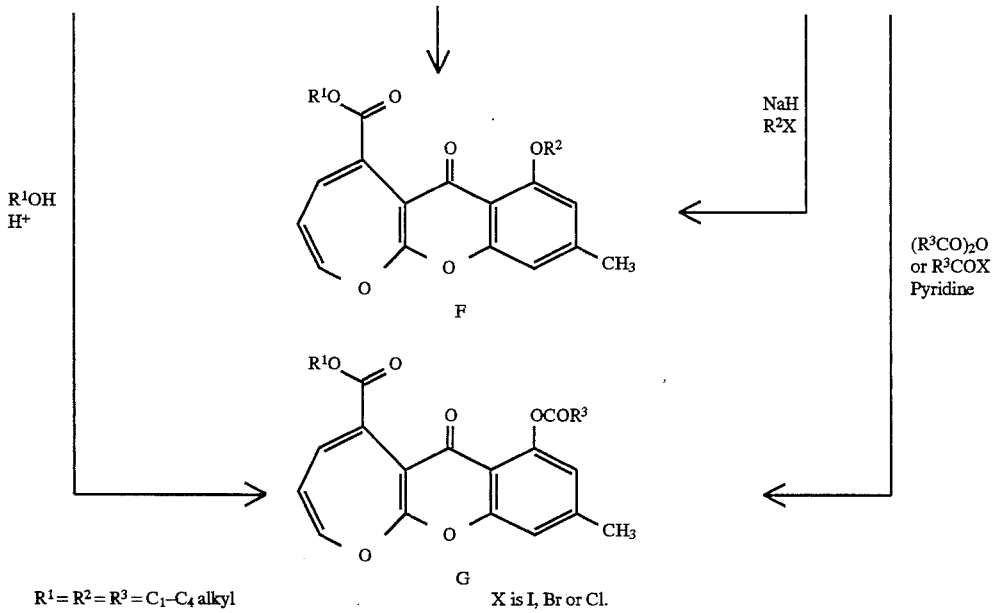

$R^1 = R^2 = R^3 = C_1-C_4$ alkyl

X is I, Br or Cl.

The methyl ester of the compound A of the instant invention may be easily hydrolyzed by using standard hydrolytic conditions, such as potassium carbonate in aqueous methanol, sodium hydroxide in water and the like to give acid B which could subsequently be converted into compounds C by Fisher esterification using desired alcohols. Acylation of compound B with standard acylating reagent, such as acetic anhydride in pyridine, acyl chloride in pyridine and the like, will produce compound D which in turn could be esterified using Fisher esterification with appropriate alcohols to give compound G. Compound G could also be prepared from compound C by using the acylation procedures mentioned above. The acid group of compound B could be protected with a compatible protecting group, such as benzyl ester, and then reacted with a suitable base, such as sodium hydride or potassium carbonate, and appropriate alkyl halides, e.g. methyl iodide, to give ester protected compound E, which, upon deprotection using standard conditions such as hydrogenolysis or basic hydrolysis, will give compound E. Alkylation of compound C, using a suitable base, such as sodium hydride or potassium carbonate, and alkyl halide, e.g. methyl iodide, will produce compound F.

REACTION SCHEME B

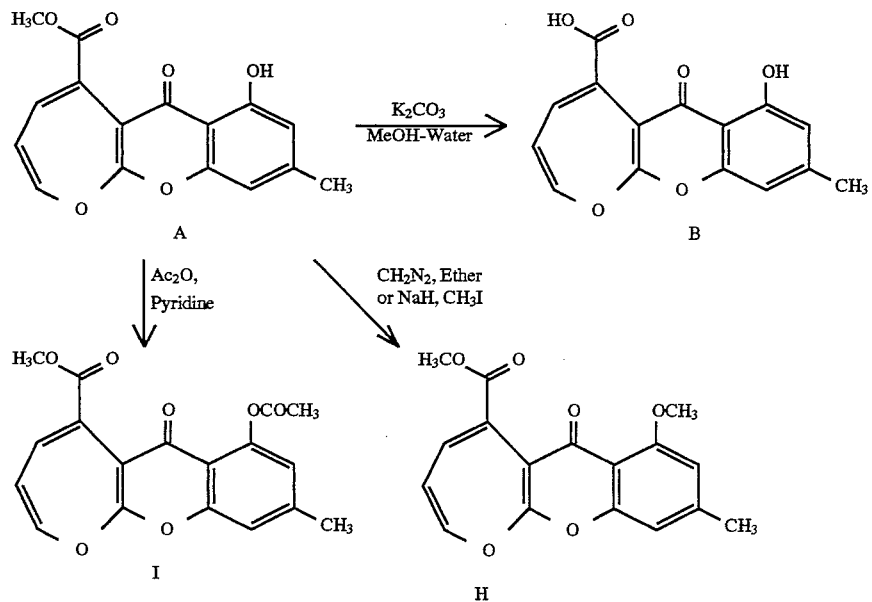

The specific compounds of the instant invention may be derivatized as illustrated in the Reaction Scheme B. Compound A, which is obtained by the fermentation as described herein above, could be acylated under standard conditions, such as acetic anhydride in pyridine, acetyl chloride in pyridine and the like, to provide acetylated Compound H. Treatment of Compound A with a methylating reagent, such as diazomethane and the like, provides the methyl ether methyl ester H. The methyl ester A could be hydrolyzed using standard hydrolytic condition, such as potassium carbonate in aqueous methanol, sodium hydroxide in water and the like to give the acid, Compound B, which can serve as an intermediate in the synthesis of compounds such as Compounds H and I.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethyl-ammonium hydroxide. The salts included herein encompass those wherein the methyl ester of the compounds of formula I is hydrolyzed to the carboxylic acid and then reacted with the appropriate base to form the above salts using standard methods known in the art.

The hydrates of the compounds of formula I are included within the scope of the invention. The compounds may form mono-, di-, trihydrates, etc.

Also included within the scope of this invention are prodrug forms of the compounds of formula I. A prodrug is a compound which results from a chemical modification of a biologically active compound that will liberate the active compound in vivo due to enzymatic or hydrolytic cleavage. (*Modern Pharmaceuticals*, 2d ed., vol. 40, p. 861, 1990.) Compounds of the instant invention may form prodrug esters of the acid or hydroxyl moiety.

The examples provided herein are intended to assist in a further understanding of the invention. Particular materials employed, species and conditions are intended to be further illustrative of the invention and not limitative of the reasonable scope thereof.

EXAMPLE 1

7-hydroxy-9-methyl-6-oxo-6H-oxepino[2,3-b][1] benzopyran-5-carboxylic acid methyl ester
(Compound A)

Step A: Preparation of Seed Culture MF6118

MF 6118 cultures were maintained as mixtures of spores and hyphae in sterile soil and stored at 4° C. until ready for use. Seed cultures were inoculated by using a small portion of the preserved soil aseptically transferred into a 250 ml Erlenmeyer flask containing 50 ml of seed medium of the following composition (in g/liter); corn steep liquor, 5.0; tomato paste, 40.0; oat flour, 10.0; glucose, 10.0; and trace elements solution, 10 ml/liter (consisting of, in g/liter: $FeSO_4 \cdot 7H_2O$, 1.0; $MnSO_4 \cdot 4H_2O$, 1.0; $CuCl_2 \cdot 2H_2O$, 0.025; $CaCl_2 \cdot 2H_2O$, 0.1; $H_3BO_3$, 0.056; $(NH_4)_6Mo7O_{24} \cdot 4H_2O$, 0.019; $ZnSO_4 \cdot 7H_2O$, 0.2; dissolved in 0.6N HCl). The pH of the medium was adjusted to 6.8 by addition of NaOH before sterilization. Seed medium was prepared using distilled water and was dispensed into Erlenmeyer flasks that were capped with cotton plugs before being autoclaved at 121° C. for 20 minutes. Seed cultures were incubated at 25° C., on a gyrotory shaker (220 rpm, 5.1 cm throw) for 72–73 hours prior to inoculation of fermentation production flasks.

Step B: Preparation of Production Culture from Seed Culture MF6118

Production fermentations were performed in 250 ml Erlenmeyer flasks containing 44 ml of liquid production medium formulated as follows: corn meal 50.0 gm, sucrose 80.0 gm, yeast extract 1.0 gm and distilled water to 1 liter. Liquid medium production flasks were capped with cotton plugs and sterilized at 121° C. for 15 minutes. Each production flask was inoculated with 2.0 ml vegetative seed growth. Production flasks were incubated one third at 22° C., one third at 25° C., and one third at 27° C. on a gyrotory shaker (220 rpm, 5.1 cm throw) for 17 days. At harvest each flask was extracted with 50 ml. methyl ethyl ketone (MEK). The liquid from all harvested flasks were combined and used for product isolation.

Step C: Isolation and Purification of 7-hydroxy-9-methyl-6-oxo-6H-oxepino[2,3-b][1]benzopyran-5-carboxylic acid methyl ester The fermentation described in Example 1 (MF 6118) of Phoma sps. (0.78 L) was grown for 17 days and extracted twice with 1 L each of methyl ethyl ketone by shaking the flasks for 2 hrs on a shaker. The extract was collected by filtration through a bed of Celite. Methyl ethyl ketone was removed under reduced pressure by distillation using a rotatory evaporator and finally lyophilized to give 4.5 gm of solid. The solid was triturated with 200 mL of methanol and filtered to give filtrate A and undissolved solid. The undissolved solid was heated in 1:1 ethyl acetate and acetone (200 mL) and filtered to give filtrate B and a insoluble residue. The filtrate B was slowly concentrated under reduced pressure to give thick yellowish cyrstals of compound A which was collected by filtration. Significant amount of compound A was also present in the filtrate A and was purified by a chromatography on a 2.0 L Sephadex LH-20 column. Elution of the column with methanol followed by tritration with methanol and filtration gave additional amounts of compound A.

$^1$H NMR 400 MHz, ($CDCl_3$), δ: 2.40 (3H, t, J=0.4 Hz, $CH_3$), 3.82 (3H, s, $OCH_3$), 5.87 (1H, t, J=5.6 Hz, =CH), 6.36 (1H, d, J=5.6 Hz, =CH), 6.65 (1H, dq, J=1.6, 0.8 Hz, ArCH), 6.66 (1H, dq, J=1.2, 0.4 Hz, ArCH), 6.94 (1H, d, J=5.6 Hz, =CH), 12.05 (1H, s, OH).

$^{13}$C NMR 400 MHz, ($CDCl_3$), δ: 22.39 ($CH_3$), 52.50 ($OCH_3$), 104.77 (qC), 107.26 (2×qC), 113.29 (CH), 116.44 (CH), 130.80 (qC), 131.93 (CH), 146.71 (CH), 147.49 (qC), 153.63 (qC), 160.54 (qC), 161.72 (qC), 166.94 (qC), 182.26 (qC).

MS (HREI): m/z 300.0629 ($M^+$, Calc'd for FOR $C_{16}H_{12}O_6$: 300.0634).

EXAMPLE 2

7-hydroxy-9-methyl-6-oxo-6H-oxepino[2,3-b][1] benzopyran-5-carboxylic acid methyl ester
(Compound A)

The method for production of the titled compound involves inoculating the seed culture as described in Example 1, Step A, into the production medium of Example 1, Step B, and then incubating the inoculated production flasks at 22° C. on a gyrotory shaker (220 rpm, 5.1 cm throw) for 15 days. At harvest, each flask was extracted with 50 ml MEK (agitation 220 rpm at 27 degrees for 45 minutes) in preparation for assay of the MEK layer. This is followed by the isolation and purification of the compound, as described in Example 1, Step C. Following the procedure of Example 1, Step C, the titled compound is isolated and purified.

EXAMPLE 3

7-hydroxy-9-methyl-6-oxo-6H-oxepino[2,3-b][1]benzopyran-5-carboxylic acid (Compound B)

Hydrolyzing the product of Example 1 with potassium carbonate in aqueous methanol, followed by acidification with dilute acid, the titled compound is prepared.

EXAMPLE 4

7-methoxy-9-methyl-6-oxo-6H-oxepino[2,3-b][1]benzopyran-5-carboxylic acid methyl ester (Compound H)

Reacting the product of Example 1 in methylene chloride with diazomethane, the titled compound is prepared.

EXAMPLE 5

7-acetyloxy-9-methyl-6-oxo-6H-oxepino[2,3-b][1]benzopyran-5-carboxylic acid methyl ester (Compound I)

Reacting the product of Example 1 with pyridine and acetic anhydride, the titled compound is prepared.

What is claimed is:

1. A compound of formula I:

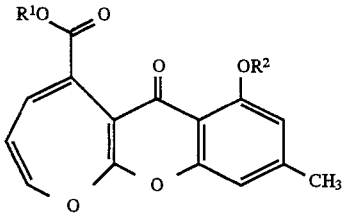

wherein:

$R^1$ is H, or $C_1$-$C_4$ alkyl;
$R^2$ is H, $C_1$-$C_4$ alkyl, or —C(=O)$R^3$; and
$R^3$ is $C_1$-$C_4$ alkyl;

or the pharmaceutically acceptable salt, hydrate or prodrug thereof.

2. The compound according to claim 1, which has the formula:

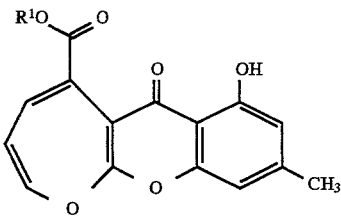

$R^1$ is H, or $C_1$-$C_4$ alkyl;

or the pharmaceutically acceptable salt, hydrate or prodrug thereof.

3. The compound according to claim 1, which has the formula:

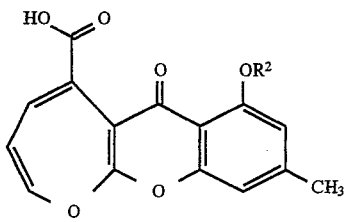

$R^2$ is H, $C_1$-$C_4$ alkyl, or —C(=O)$R^3$; and
$R^3$ is $C_1$-$C_4$ alkyl;

or the pharmaceutically acceptable salt, hydrate or prodrug thereof.

4. A compound of formula:

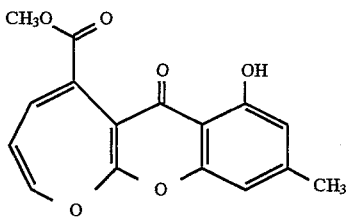

or the pharmaceutically acceptable salt, hydrate or prodrug thereof.

5. A compound of formula:

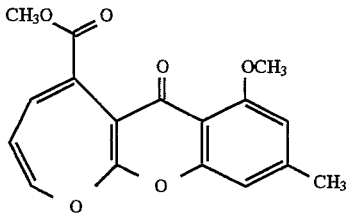

or the pharmaceutically acceptable hydrate.

6. A compound of formula:

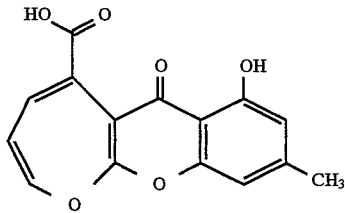

or the pharmaceutically acceptable salt, hydrate or prodrug thereof.

7. A compound of formula:

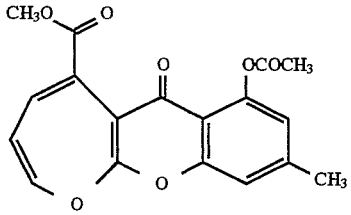

or the pharmaceutically acceptable hydrate thereof.

8. A pharmaceutical composition useful for the treatment of cancer, comprising a pharmaceutically acceptable carrier, and dispersed therein, and a chemotherapeutically effective amount of a compound of claim 1.

9. A method for treating cancer comprising the administration of a chemotherapeutically effective amount of a composition of claim 8 to a mammal in need of such treatment.

10. A method for the inhibition of farnesyl-protein transferase comprising the administration of a chemotherapeutically effective amount of a composition of claim 8 to a mammal in need of such treatment.

11. A method for inhibiting farnesylation of Ras protein comprising the administration of a chemotherapeutically effective amount of a composition of claim 8 to a mammal in need of such treatment.

* * * * *